(12) United States Patent
Yun et al.

(10) Patent No.: US 8,047,088 B2
(45) Date of Patent: Nov. 1, 2011

(54) ENVIRONMENTAL TEST CHAMBER HAVING MOVABLE PANEL AND METHOD OF DRIVING THE SAME

(75) Inventors: Kwang-su Yun, Gwangju-si (KR); Chong-hee Yu, Gwangju-si (KR); Jai-sang Koh, Gwangju-si (KR)

(73) Assignee: Electronics and Telecommunications Research Institute (KR)

( * ) Notice: Subject to any disclaimer, the term of this patent is extended or adjusted under 35 U.S.C. 154(b) by 110 days.

(21) Appl. No.: 12/618,574

(22) Filed: Nov. 13, 2009

(65) Prior Publication Data
US 2010/0154571 A1 Jun. 24, 2010

(30) Foreign Application Priority Data
Dec. 19, 2008 (KR) .......................... 10-2008-0130680

(51) Int. Cl.
*G01N 17/00* (2006.01)
(52) U.S. Cl. ....................................................... 73/865.6
(58) Field of Classification Search .................. 73/865.6
See application file for complete search history.

(56) References Cited

U.S. PATENT DOCUMENTS

| | | | | |
|---|---|---|---|---|
| 2002/0056377 A1* | 5/2002 | Gawley et al. | ................... | 100/35 |
| 2003/0121337 A1* | 7/2003 | Wanek et al. | ................ | 73/865.6 |
| 2006/0150755 A1* | 7/2006 | Johnson | ....................... | 73/865.6 |

FOREIGN PATENT DOCUMENTS

| KR | 10-2000-0034075 A | 6/2000 |
|---|---|---|
| KR | 10-2003-0000182 A | 1/2003 |

* cited by examiner

*Primary Examiner* — Hezron E Williams
*Assistant Examiner* — Gregory J Redmann
(74) *Attorney, Agent, or Firm* — Blakely, Sokoloff, Taylor & Zafman (57) ABSTRACT

Disclosed are an environmental test chamber having a movable panel and a method of driving the same. The environmental test chamber is used in a thermo-hygrostat, a thermostat, and a high temperature-low temperature tester. The chamber body includes a test cavity in which an object is disposed. An air-conditioning unit conditions the air inside the test cavity, thereby controlling a condition of the test cavity. A movable panel is accommodated in the chamber body to decrease or increase a volume of the test cavity. The efficiency of the chamber is enhanced, and the cost and space required for installing additional equipment is reduced.

17 Claims, 8 Drawing Sheets

ENVIRONMENTAL TEST CHAMBER HAVING MOVABLE PANEL AND METHOD OF DRIVING THE SAME

CROSS-REFERENCE TO RELATED APPLICATION

This application claims the benefit under 35 U.S.C. §119 (a) of Korean Patent Application No. 10-2008-0130680, filed on Dec. 19, 2008, the disclosure of which is incorporated by reference in its entirety for all purposes.

BACKGROUND

1. Field

The following description relates to an environmental test chamber having a movable panel and a method of driving the same, and more particularly to an environmental test chamber having a movable panel, which can be used in a thermo-hygrostat, a thermostat, and a high temperature-low temperature tester, and a method of driving the same.

2. Description of the Related Art

In general, an environmental test chamber is used on an apparatus such as a thermo-hygrostat, a thermostat, and a high temperature-low temperature tester. The interior of the environmental test chamber needs to be maintained at a predetermined temperature and humidity to form a test environment suitable for an object to be tested.

Figure 1:
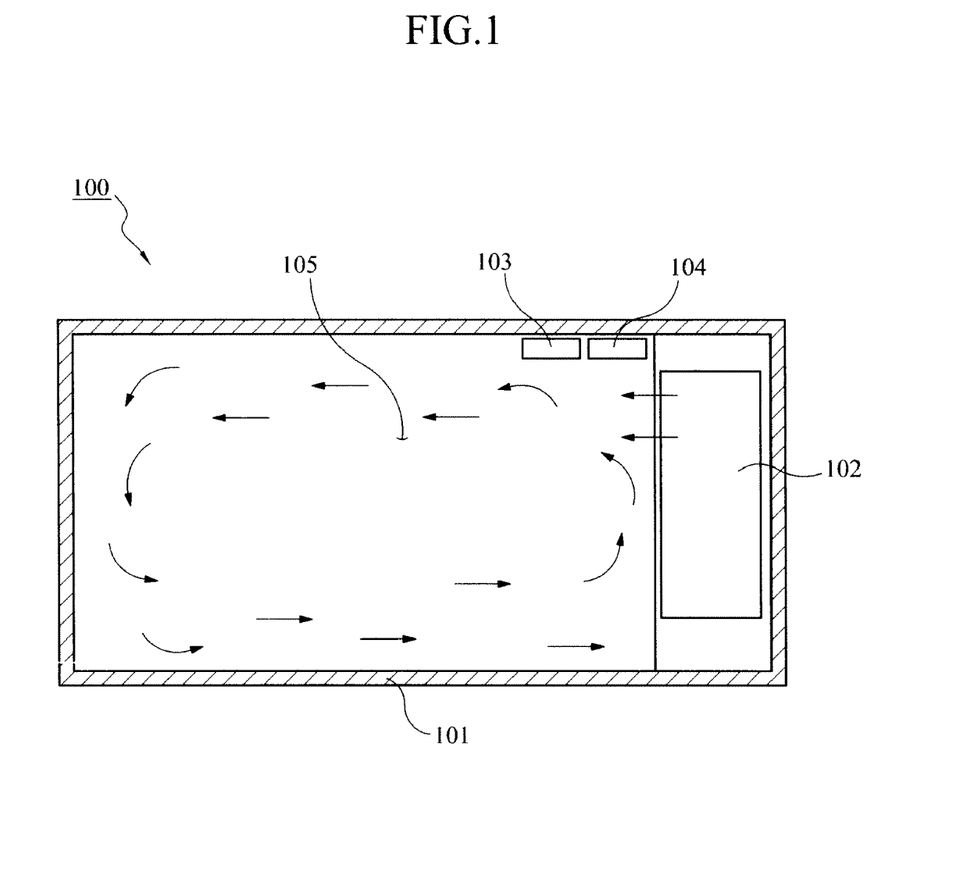
FIG. 1 is a sectional view showing a chamber body of an environmental test chamber according to the related art.

FIG. 1 is a sectional view schematically showing a chamber body of a conventional environmental test chamber. As shown in FIG. 1, the conventional environmental test chamber 100 includes a chamber body 101, an air-conditioning unit 102, a temperature sensor 103 and a humidity sensor 104.

The chamber body 101 forms the external appearance of the environmental test chamber 100, and includes a test cavity 105 in which an object is disposed. The air-conditioning unit 102 is provided with a heater, an evaporator, a condenser, a compressor, an expansion valve, a reheating coil and a blower, etc. The air-conditioning unit 102 controls the temperature and humidity of the test cavity 105 by heating, cooling, humidifying and dehumidifying air of the test cavity 105. The temperature sensor 103 and the humidity sensor 104 detect the temperature and humidity of the test cavity 105.

The efficiency of controlling the temperature and humidity of the test cavity depends on the volume of the test cavity. That is, a small sized object such as optical components is preferred to be tested in a relative small test cavity, and a large sized object is preferred to be tested in a relative large test cavity. However, in a conventional environmental test chamber, the test cavity has a limited volume. This is because the conventional test cavity has fixed walls.

Accordingly, the conventional environmental test chamber needs to be manufactured in various sizes to satisfy requirements of different objects. In addition, if higher performance of the chamber is required, equipment installed in the chamber such as the heater, evaporator, condenser, compressor and expansion valve are replaced with other pieces of equipment which meet higher requirements.

SUMMARY

Accordingly, in one aspect, there is provided an environmental test chamber, having a test cavity with an adjustable volume.

In one general aspect, there is provided an environmental test chamber for forming a test environment suitable for an object by controlling a temperature and humidity inside the test chamber. The environmental test chamber includes a chamber body provided therein with a test cavity where the object is disposed; an air-conditioning unit to condition the air inside the test cavity, thereby controlling a condition of the test cavity; and a movable panel accommodated in the chamber body to decrease or increase a volume of the test cavity.

The movable panel moves along inner walls of the chamber body.

The environmental test chamber further includes a panel driving part coupled to a side of the movable panel to drive the movable panel.

The panel driving part includes a first support part supported by one of the inner walls of the chamber body which faces the movable panel; a second support part supported by a side of the movable panel; a sliding member slidably connected to one of the first support part and the second part; and a variable spacer which is configured to change an interval between the first support part and the second support part, wherein the variable spacer has a first end connected to the sliding member and a second end connected to one of the first support part and the second support part which is not connected to the sliding member.

The variable spacer includes a pair of cross bars, middle parts of which are rotatably connected to each other.

The first support part and the second guide part have guide rods, respectively. A power unit including a motor is coupled to at least one of the first support part and the second support part, and wherein the interval between the first support part and the second support part changes as an end of the respective cross bars slides along the guide rods.

The power unit is provided with a screw to convert a rotary motion to a linear motion, and the sliding member is connected to the screw.

The movable panel is provided with a sealing part to keep the test cavity airtight.

The environmental test chamber further includes an air-tightness driving part to allow the sealing part to closely adhere to at least one of the inner walls of the chamber body or to release the sealing part.

The air-tightness driving part includes an insertion bar coupled to the sealing part; a rod part connected to the insertion bar; and an operation part, which is connected to the rod part, and wherein if the operation part operates in a first direction, the rod part allows the sealing part to closely adhere to the inner walls of the chamber body, and if the operation part operates in a second direction different from the first direction, the rod part releases the sealing part.

A plurality of each of the sealing part and the insertion bar are disposed on the respective inner walls of the chamber body. The rod part presses or releases the insertion bar according to rotation of the operation part.

The road parts are connected to each other in a stepped shape to prevent interference with to each other.

The environmental test chamber further includes a flexible bellows configured to connect an inside of the test cavity to an outside of the chamber body, wherein the flexible bellows expands and contracts as the movable panel moves, and thus changes in a length.

The environmental test chamber further includes a guide part including a roller used to guide the movable panel.

In another general aspect, there is provided a method of driving an environmental test chamber. The method is performed as follows. A desired volume of the test cavity where an object is disposed is set. The panel driving part is operated to drive the movable panel along inner walls of the chamber body such that the test cavity has the desired volume. The test cavity is kept airtight by operating the air-tightness driving part. An environmental test is performed by operating the air-conditioning unit.

In the driving of the movable panel, a screw serving as a power unit rotates, an end of respective cross bars connected to the screw slides, and middle parts of the respective cross bars rotate such that an interval between a first support part supported by the inner wall of the chamber body, which faces the movable panel, and a second support part supported by a side of the movable panel changes.

In the keeping of the test cavity air-tightness, an operation part is rotated, an insertion bar is pressured by a rod part due to rotation of the operation part, and thus the sealing part coupled to the insertion bar closely adheres to the inner walls of the chamber body.

According to the present invention, when components requiring a strict test environment are tested, the volume of the test cavity is reduced to form a volume suitable for the strict environment test, and thus the efficiency of the chamber can be enhanced, that is, the thermo hygrostat efficiency of the chamber is enhanced. In addition, the cost and space required for to installing additional equipment can be reduced.

Other features will become apparent to those skilled in the art from the following detailed description, which, taken in conjunction with the attached drawings, discloses exemplary embodiments of the invention.

BRIEF DESCRIPTION OF THE DRAWINGS

Elements, features, and structures are denoted by the same reference numerals throughout the drawings and the detailed description, and the size and proportions of some elements may be exaggerated in the drawings for clarity and convenience.

DETAILED DESCRIPTION

The detailed description is provided to assist the reader in gaining a comprehensive understanding of the methods, apparatuses and/or systems described herein. Various changes, modifications, and equivalents of the systems, apparatuses, and/or methods described herein will likely suggest themselves to those of ordinary skill in the art. Also, descriptions of well-known functions and constructions are omitted to increase clarity and conciseness.

Figure 2:
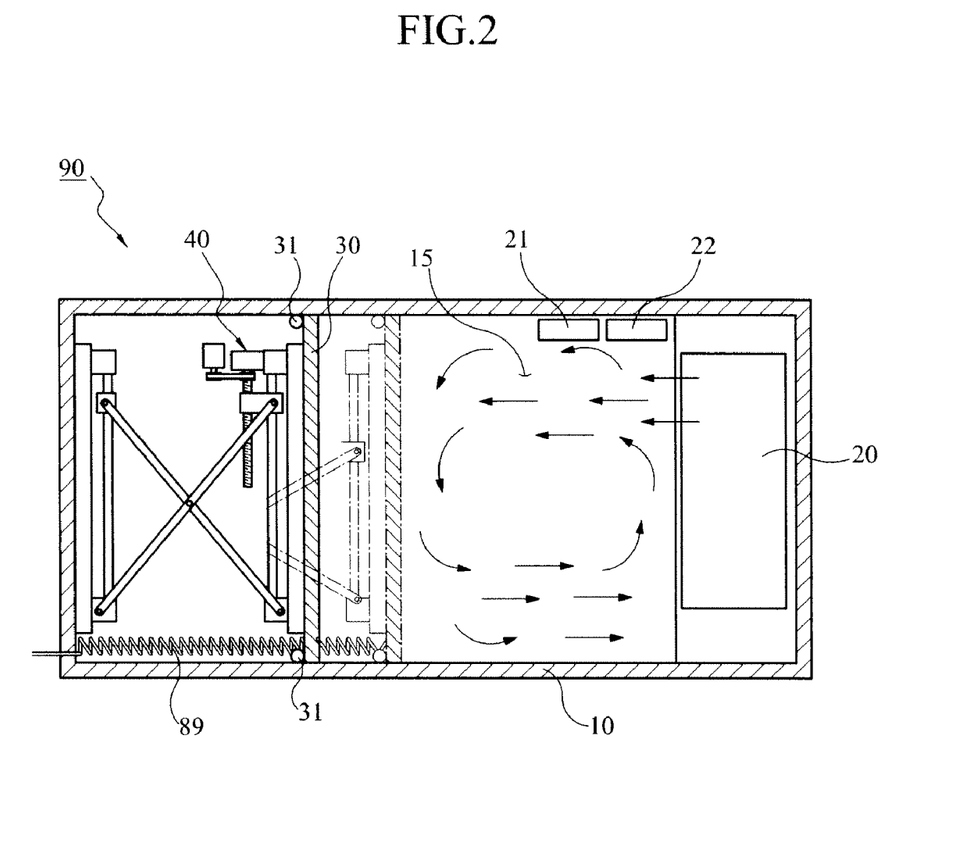
FIG. 2 is a sectional view showing a chamber body of an exemplary environmental test chamber.

FIG. 2 is a sectional view showing a chamber body of an exemplary environmental test chamber.

As shown in FIG. 2, an environmental test chamber 90 controls the temperature and humidity of the interior of the environmental test chamber 90, thereby forming a test environment suitable for an object. The environmental test chamber 90 includes a chamber body 10, an air-conditioning unit 20 and a movable panel 30.

A test cavity 15 is formed within the chamber body 10. The chamber body 10 has a frame forming an external appearance of the environmental test chamber 90. The test cavity 15 is a space where an object is disposed. The test cavity 15 is defined by inner walls of the chamber body 10. That is, the test cavity 15 has a volume corresponding to the size of the interior of the chamber body 10.

For example, the environmental test chamber 90 may be used in a thermo-hygrostat, a thermostat, and a high temperature-low temperature tester. Accordingly, the test cavity 15 creates various test environments such as a high temperature, a low temperature, a high humidity and a low humidity. The object may be a small component, such as optical components and electronic components, or a large component such as machine parts.

The air-conditioning unit 20 controls the temperature and humidity of the test cavity 15 by heating, cooling, humidifying and dehumidifying air of the test cavity 15. The air-conditioning unit 20 is provided with a heater, an evaporator, a condenser, a compressor, an expansion valve, a reheating coil, a blower, etc. Air discharged from the air-conditioning unit 20 is forcedly circulated in the test cavity 15 by the blower.

In this case, the air-conditioning unit is provided with a temperature sensor 21 and a humidity sensor 22. The temperature sensor 21 detects the temperature of the test cavity 15 and provides feedback on the temperature data. The humidity sensor 22 detects the humidity of the test cavity 15 and provides feedback on the humidity data.

The movable panel 30 serves to decrease or increase the volume of the test cavity 15. Different from a conventional test cavity, the test cavity 15 according to the present invention has a variable volume. In detail, the movable panel 30 installed inside the chamber body 10 allows a volume of the test cavity 15 to be changed.

The movable panel 30 is installed inside the chamber body 10 to serve as an inner wall of the chamber body 10. That is, the movable panel 30 divides the interior of the chamber body 10, thereby forming a space in the chamber body 10. The test cavity 15 is provided in the spacer formed by the movable panel 30. Accordingly, as the movable panel 30 moves inside the chamber body 10, a volume of the test cavity 15 is decreased or increased.

Since the test cavity 15 has a variable volume, the performance of the test cavity 15 is improved when tests such as a temperature test or a humidity test are performed. Such a movable panel structure may increase the efficiency of use of equipment such as the air-conditioning unit 20 without changing the size of the chamber body 10. That is, when a predetermined object needs to be subject to a strict test environment, the volume of the test cavity 15 is reduced to be suitable for the test environment, thereby obtaining improved test performance. As a result, an additional chamber does not need to be installed and equipment such as the air-conditioning unit 20 does not need to be replaced with equipment meeting higher requirements, and thus reduces the cost and time required for performing a test.

In addition, the movable panel 30 is installed to move along the inner wall of the chamber body 10.

In this case, the chamber body 10 may have a guide part. The guide part is installed on the inner wall of the chamber body 10 to guide the movable panel 30. The guide part may be provided in the form of a single roller or a plurality of rollers 31. Alternatively, the guide part may be provided in the form of a guide rail and a guide groove.

Meanwhile, the environmental test chamber 90 may further include a panel driving part 40. The panel driving part 40 is coupled to one side of the movable panel 30 to drive the movable panel 30.

Figure 3:
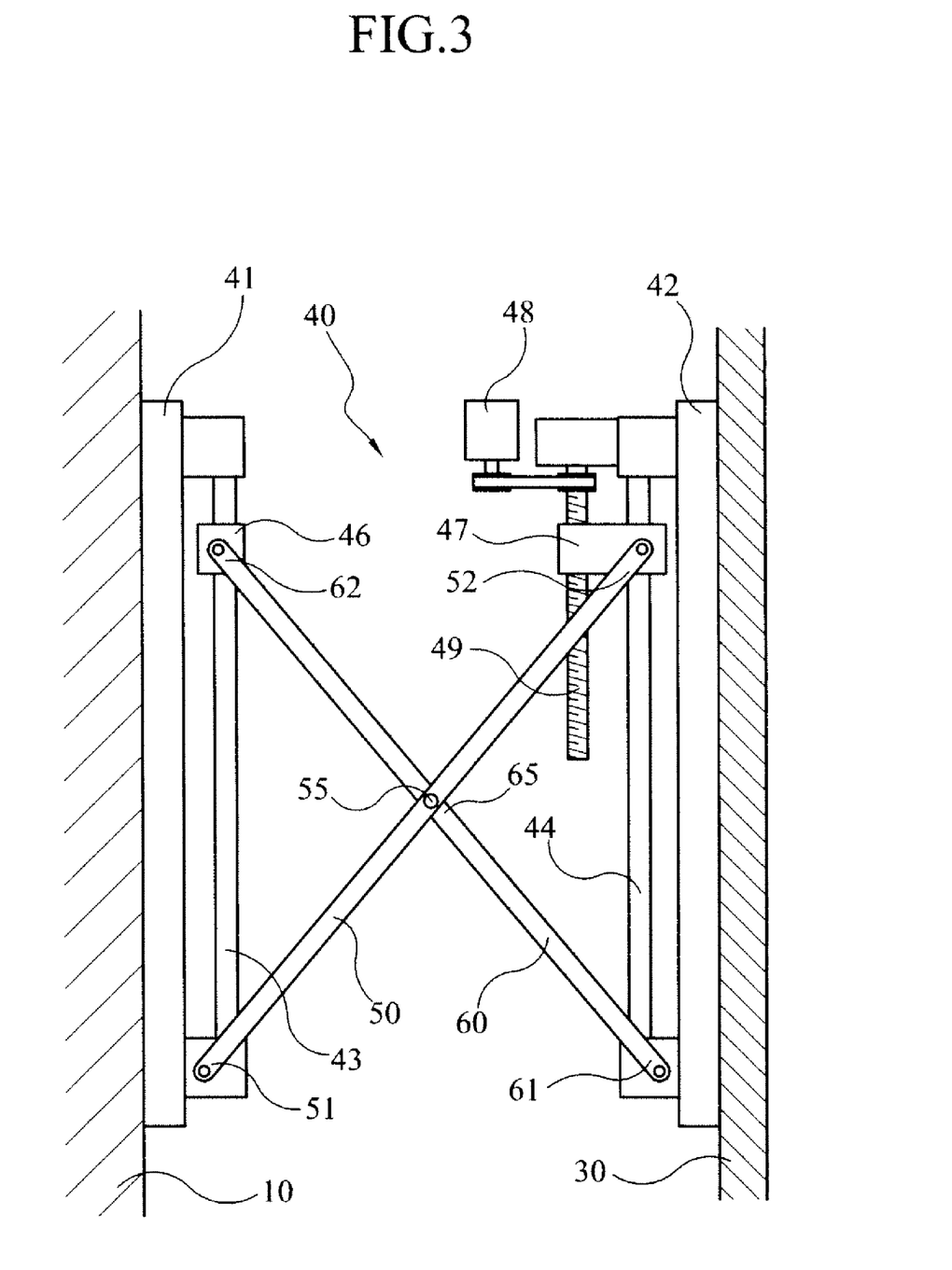
FIG. 3 is a sectional view schematically showing a panel driving part of the chamber body of FIG. 2.

FIG. 3 is a sectional view schematically showing a panel driving part of the chamber body of FIG. 2.

As shown in FIG. 3, the panel driving part 40 includes a first support part 41, a second support part 42, and cross bars including a first cross bar 50 and a second cross bar 60.

The first support part 41 is supported by one side of the inner walls of the chamber body 10, and the second support part 42 is supported by the movable panel 30.

The cross bars 50 and 60 form a pair. Two ends of each cross bars 50 and 60 are respectively connected to the first support part 41 and the second support part 42. The first cross bar 50 has a first end 51 connected to the first support part 41 and a second end 52 connected to the second support part 42. Similarly, the second cross bar 60 has a first end 61 connected to the second support part 42 and a second end 62 connected to the first support part 41. The first cross bar 50 has a middle part 55 rotatably connected on a middle part 65 of the second cross bar 60. Accordingly, as the first cross bar 50 and the second cross bar 60 rotate while crossing each other, an interval between the first support part 41 and the second support part 42 changes.

The first support 41 and the second 42 may be provided with a guide rod 43 and a guide rod 44, respectively. A power unit may be coupled to at least one of the first support part 41 and the second support part 42. The power unit is used to generate torque. The power unit may be arms of an operator or an electric motor such as a stepping motor. Preferably, the power unit may be a motor 48.

If the motor 48 serves as the power unit, the power unit may has a screw 49 to which a sliding member 47 is connected. As the motor 48 operates, the screw 49 rotates and the sliding member 47 linearly moves. The sliding member 47, which is inserted around the guide rod 44, is slidably moved. The second end 52 of the first cross bar 50 is rotatably connected to the sliding member 47. In addition, the sliding member 46, which is inserted around the guide rod 43, is slidably moved. The second end 62 of the second cross bar 60 is rotatabley connected to the sliding member 46. Meanwhile, the first end 51 of the first cross bar 50 and the second end 61 of the second cross bar 60 are rotatably connected to the first support part 41 and the second support part 42, respectively.

Figure 4:
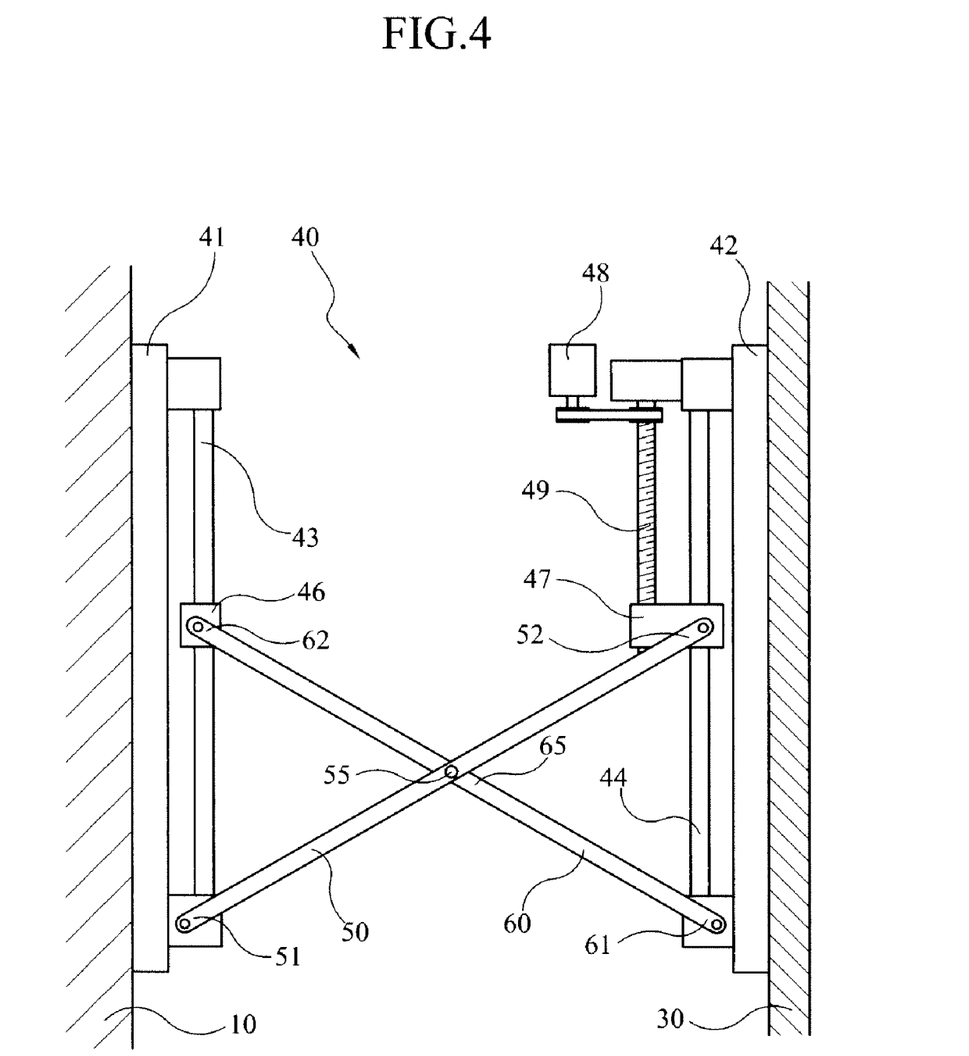
FIG. 4 is a sectional view showing an operation of the panel driving part shown in FIG. 3.

FIG. 4 is a sectional view showing an operation of the panel driving part shown in FIG. 3.

As shown in FIG. 4, when power is applied to the motor 48, the screw 49 rotates in one direction, the sliding member 47 is guided along the guide rod 44 and linearly slides downward. The first cross bar 50 connected to the sliding member 47 is forced to rotate clockwise, and the second cross bar 60 connected rotatably connected to the middle part 55 of the first cross bar 50 is forced to rotate countclockwise. Accordingly, the sliding members 46 and 47 move downward, and the first support part 41 and the second support part 42 move away from each other.

Since the first support part 41 is supported by the inner wall of the chamber body 10 and the second support part 42 is supported by the movable panel 30, the movable panel 30 moves right. As a result, a volume of the test cavity 15 is decreased. In addition, in order to increase the volume of the test cavity 15, the opposite to the above action is performed.

Such a driving mechanism is suitable for driving a heavy object and enables a precise movement of the movable panel 30.

Figure 5:
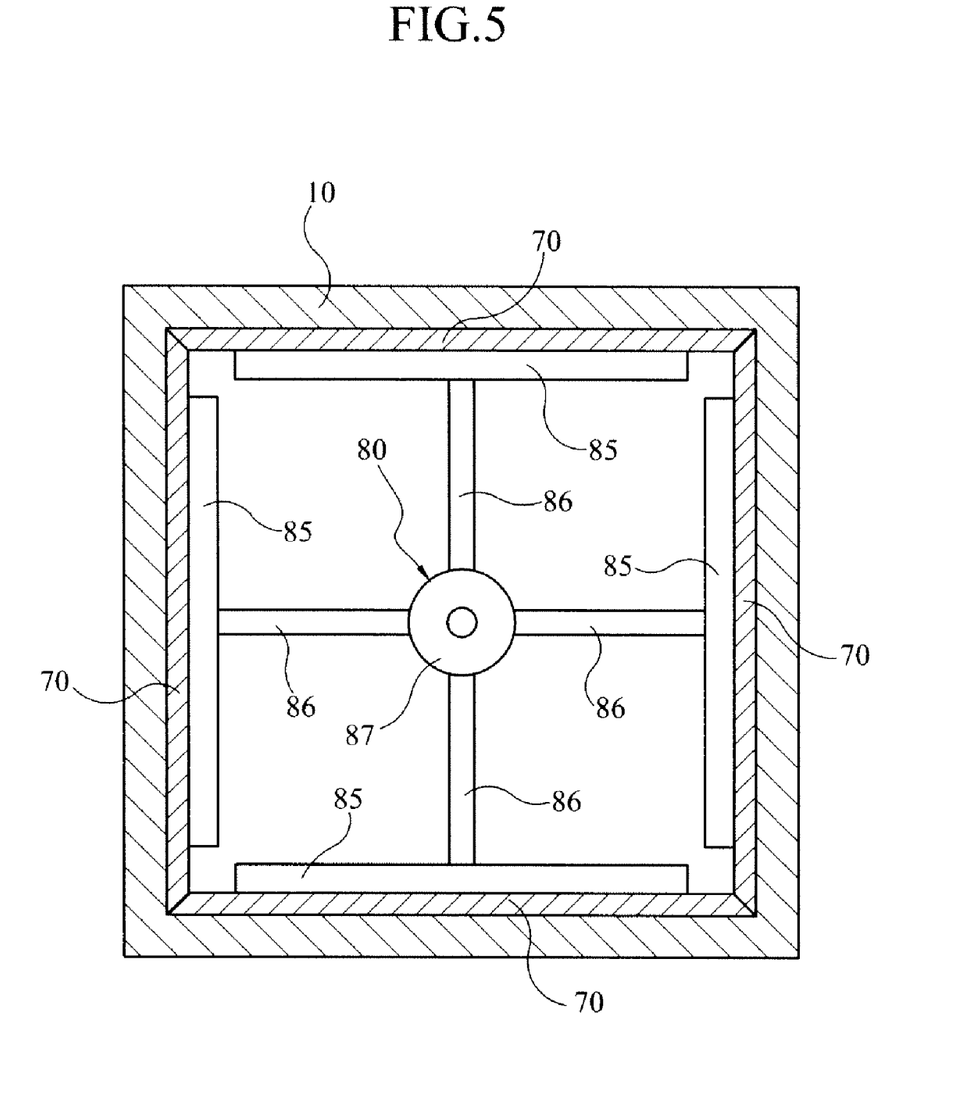
FIG. 5 is a sectional view schematically showing an air-tightness driving part of another exemplary environmental chamber.

FIG. 5 is a sectional view schematically showing an airtightness driving part of another exemplary environmental chamber.

As shown in FIG. 5, the movable panel 30 may be provided with sealing parts 70. The sealing parts 70 keep the test cavity 15 airtight. The sealing parts 70 are formed of rubber.

In this case, the environmental test chamber 90 further includes an air-tightness driving part 80. The air-tightness driving part 80 allows the sealing parts 70 to closely adhere to the inner wall of the chamber body 10 or to be released.

Figure 6A:
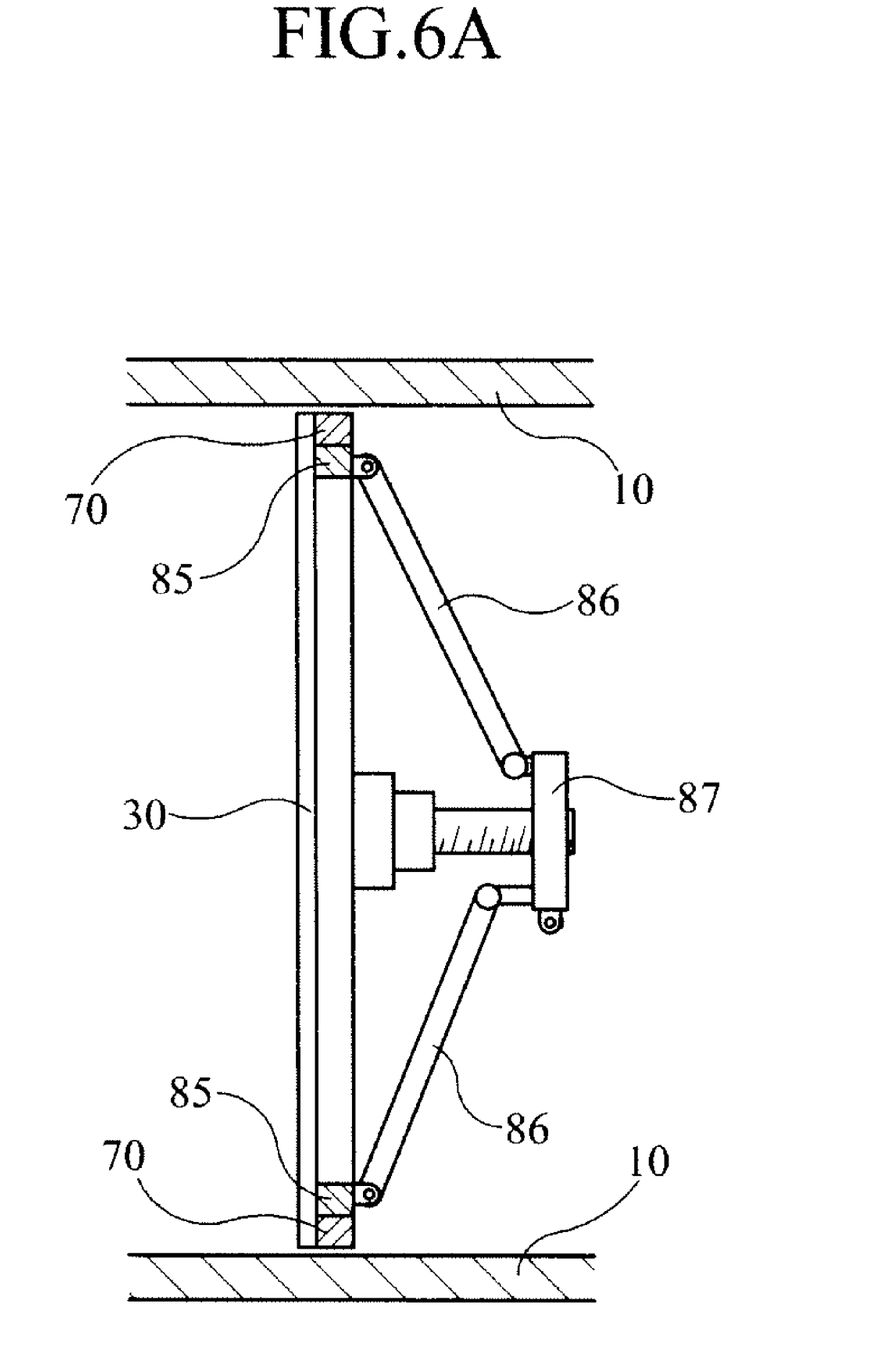
FIGS. 6A and 6B are sectional views showing an operation of the air-tightness driving part shown in FIG. 5.
Figure 6B:
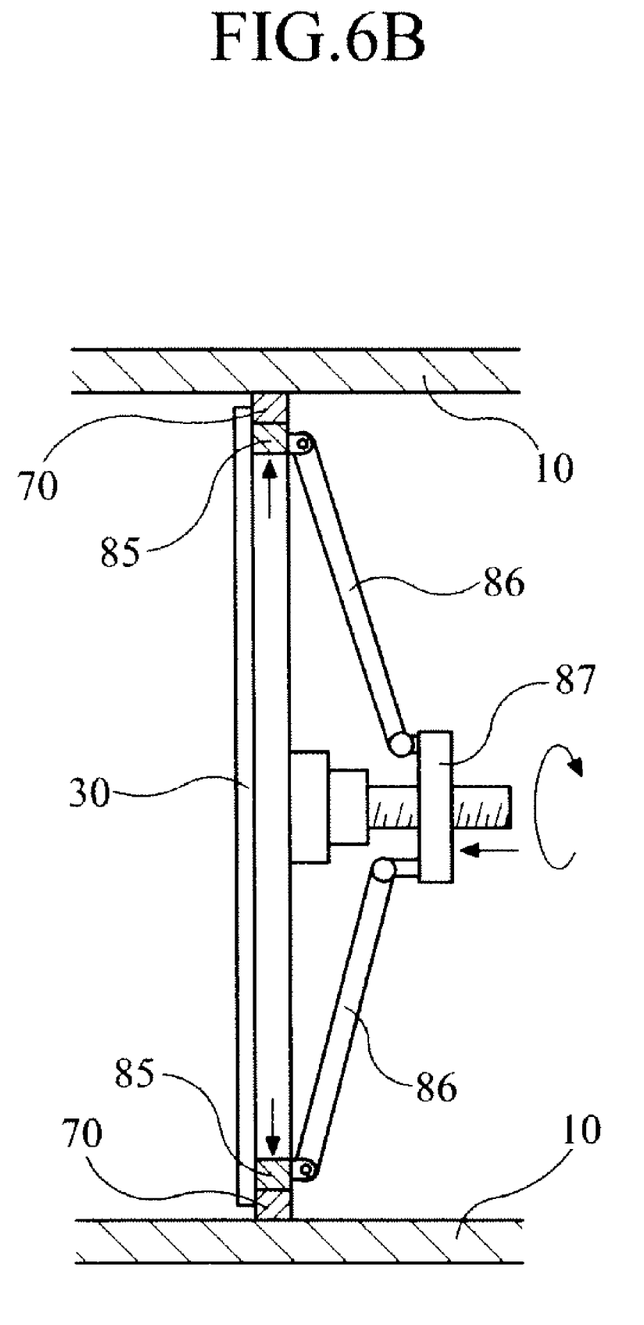

FIGS. 6A and 6B are sectional views showing an operation of the air-tightness driving part shown in FIG. 5.

As shown in FIGS. 6A and 6B, the air-tightness driving part 80 includes insertion bars 85, rod parts 86 and an operation part 87.

The insertion bars 85 are coupled to the sealing parts 70, respectively. In addition, the rod parts 86 are connected to the insertion bars 85, respectively, and the operation part 87 is connected to the rod parts 86. If the operation part 87 operates in a first direction, the rod parts 86 allow the sealing parts 70 to closely adhere to the inner walls of the chamber body 10. In addition, if the operation part 87 operates in a second direction different from the first direction, the rod parts 86 release the sealing parts 70 such that the sealing parts 70 are separated from the inner wall of the chamber body 10.

Preferably, the sealing parts 70 and the insertion bars 85 are disposed on the respective inner walls of the chamber body 10. That is, as shown in FIG. 5, when viewed in a sectional view, the sealing parts 70 are disposed at an upper part, a lower part, a left part and a right part of the chamber body 10, and the insertion bars 85 are connected to the respective sealing parts 70. The insertion bars 85 are connected to the rod parts 86 through brackets, respectively. The rod parts 86 extend inward and are rotatably connected to the operation part 87. Accordingly, the rod parts 86 press or release the insertion bars 85 when the operation part 87 rotates.

As shown in FIGS. 6A and 6B, the rod parts 86 are disposed at an upper part, a lower part, a left part and a right part on the operation part 87 such that all of the sealing parts 70 effectively adhere to the inner walls of the chamber body 10. Different from the rod parts 86 shown in FIGS. 6A and 6B, other exemplary rod parts may be disposed at an upper side and a lower side on the operation parts 87.

The rod parts 86 are connected to each other in a stepwise manner to prevent interference with each other.

Accordingly, the air tightness driving part 80 allows the sealing parts 70 to be slightly separated from the inner walls of the chamber body 10 such that the movable panel 30 moves along the inner walls of the chamber body 10. In addition, after the movement of the air-tightness driving part 80 has been completed, the air-tightness driving part 80 allows the sealing parts 70 to be pressed against the inner walls of the chamber body 10, thereby maintaining airtightnes of the test cavity 15.

Meanwhile, the environmental test chamber 90 may further include a flexible bellows (89 in FIG. 2). The flexible bellows 89 connects the inside of the test cavity 15 to the outside of the chamber body 10. The flexible bellows 89 expands and contracts as the movable panel 30 moves, so that the length of the flexible bellows 89 varies. For example, when an object provided in the test cavity 15 is tested, data signal and electric power may need to be supplied to the test cavity 15 from outside of the chamber body 10. The flexible bellows 89 is installed between the movable panel 30 and an outer wall of the chamber body 10 and has an opening which faces the outside Hereinafter, a method of driving an environmental test chamber will be described with reference to accompanying drawings.

Figure 7:
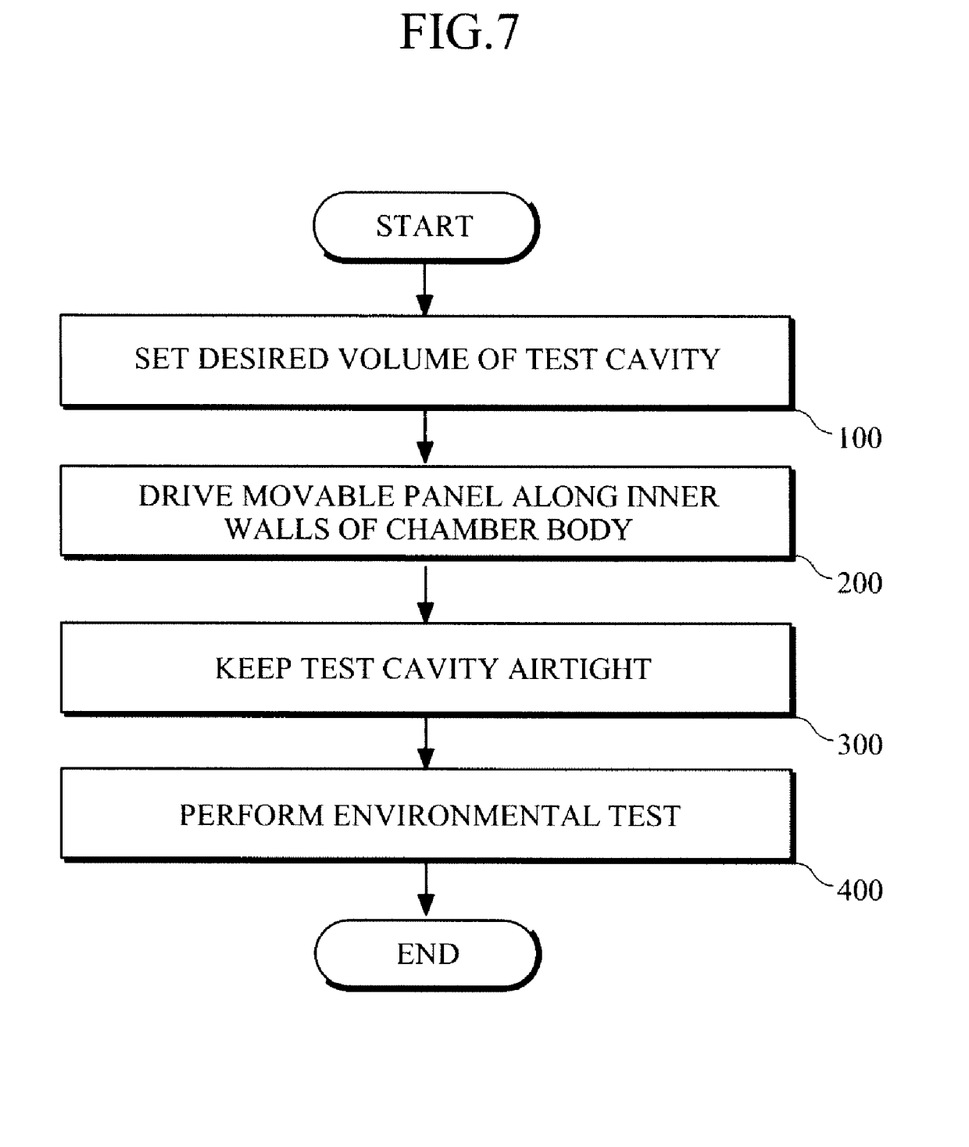
FIG. 7 is a flow chart showing a method of driving another exemplary environmental test chamber.

FIG. 7 is a flow chart showing a method of driving another exemplary environmental test chamber.

As shown in FIG. 7, the method of driving the environmental test chamber includes setting a desired volume of the test cavity (operation 100), driving the movable panel along the inner walls of the chamber body (operation 200), keeping the test cavity airtight (operation 300) and performing an environmental test (operation 400).

As shown FIGS. 1 to 6, in operation 100, the test cavity 15 for disposing an object is set to have a desired volume varying with variables such as test conditions, type of object, etc.

In operation 200, the panel driving part 40 operates to move the movable panel 30 along the inner walls of the chamber body 10 such that the test cavity 15 has the desired volume set in the operation 100.

The driving of the movable panel 30 (operation 200) is performed as follows. The screw 49 serving as a power unit rotates. An end of respective cross bars 50 and 60 connected to the screw 49 slides. As the end of the respective cross bars 50 and 60 slides, the angle made by the cross bars 50 and 60 changes, so that an interval between the first support part 41 and the second support part 42 changes.

In the operation 300, the test cavity 15 is kept airtight by operating the air-tightness driving part 80.

The keeping of test cavity 15 airtight is performed as follows. The operation part 87 rotates. The rod parts 86 press the insertion bars 85 according to the rotation of the operation part 87. The sealing parts 70 coupled to the insertion bars 85 closely adhere to the inner walls of the chamber body 10.

In the operation 400, the air-conditioning unit 20 is operated to perform an environmental test.

A number of exemplary embodiments have been described above. Nevertheless, it will be understood that various modifications may be made. For example, suitable results may be achieved if the described techniques are performed in a different t order and/or if components in a described system, architecture, device, or circuit are combined in a different manner and/or replaced or supplemented by other components or their equivalents. Accordingly, other implementations are within the scope of the following claims.

What is claimed is:

1. An environmental test chamber for forming a test environment suitable for an object by controlling a temperature and humidity inside the test chamber, the environmental test chamber comprising:
   a chamber body provided therein with a test cavity where the object is disposed;
   an air-conditioning unit to condition the air inside the test cavity, thereby controlling a condition of the test cavity; and
   a movable panel accommodated in the chamber body to decrease or increase a volume of the test cavity by moving toward or away from an inner wall of the chamber body which faces the movable panel, wherein the movable panel serves as another inner wall of the chamber body.

2. The environmental test chamber of claim 1, wherein the movable panel moves along inner walls of the chamber body.

3. The environmental test chamber of claim 2, further comprising a panel driving part coupled to a side of the movable panel to drive the movable panel.

4. The environmental test chamber of claim 3, wherein the panel driving part includes:
   a first support part supported by one of the inner walls of the chamber body which faces the movable panel;
   a second support part supported by a side of the movable panel;
   a sliding member slidably connected to one of the first support part and the second part; and
   a variable spacer which is configured to change an interval between the first support part and the second support part, wherein the variable spacer has a first end connected to the sliding member and a second end connected to one of the first support part and the second support part which is not connected to the sliding member.

5. The environmental test chamber of claim 4, wherein the variable spacer includes a pair of cross bars, middle parts of which are rotatably connected to each other.

6. The environmental test chamber of claim 5, wherein the first support part and the second guide part have guide rods, respectively, and a power unit including a motor is coupled to at least one of the first support part and the second support part, and wherein the interval between the first support part and the second support part changes as an end of the respective cross bars slides along the guide rods.

7. The environmental test chamber of claim 6, wherein the power unit is provided with a screw to convert a rotary motion to a linear motion, and the sliding member is connected to the screw.

8. The environmental test chamber of claim 2, wherein the movable panel is provided with a sealing part to keep the test cavity airtight.

9. The environmental test chamber of claim 8, further comprising an air-tightness driving part to allow the sealing part to closely adhere to at least one of the inner walls of the chamber body or to release the sealing part.

10. The environmental test chamber of claim 9, wherein the air-tightness driving part includes:
    an insertion bar coupled to the sealing part;
    a rod part connected to the insertion bar; and
    an operation part, which is connected to the rod part, and wherein if the operation part operates in a first direction, the rod part allows the sealing part to closely adhere to the inner walls of the chamber body, and if the operation part operates in a second direction different from the first direction, the rod part releases the sealing part.

11. The environmental test chamber of claim 10, wherein a plurality of each of the sealing part and the insertion bar are disposed on the respective inner walls of the chamber body, and wherein the rod part presses or releases the insertion bar according to rotation of the operation part.

12. The environmental test chamber of claim 11, wherein the road parts are connected to each other in a stepped shape to prevent interference with each other.

13. The environmental test chamber of claim 2, further comprising a flexible bellows configured to connect an inside of the test cavity to an outside of the chamber body, wherein the flexible bellows expands and contracts as the movable panel moves and thus changes in length.

14. The environmental test chamber of claim 2, further comprising a guide part including a roller used to guide the movable panel.

15. A method of driving an environmental test chamber including a chamber body having a test cavity, an air-conditioning unit to condition air inside the test cavity, a movable panel to decrease or increase a volume of the test cavity, a panel driving part to drive the movable panel and an airtightness driving part to drive a sealing part, the method comprising:

setting a desired volume of the test cavity where an object is disposed;

operating the panel driving part to drive the movable panel along inner walls of the chamber body to a set distance from an inner wall of the chamber body which faces the movable panel such that the test cavity has the desired volume, wherein the movable panel serves as another inner wall of the chamber body;

keeping the test cavity airtight by operating the air-tightness driving part; and performing an environmental test by operating the air-conditioning unit.

16. The method of claim 15, wherein, in the driving of the movable panel, a screw serving as a power unit rotates, an end of respective cross bars connected to the screw slides, and middle parts of the respective cross bars rotate, such that an interval between a first support part supported by the inner wall of the chamber body, which faces the movable panel, and a second support part supported by a side of the movable panel changes.

17. The method of claim 15, wherein in the keeping of the test cavity air-tightness, an operation part is rotated, an insertion bar is pressured by a rod part due to rotation of the operation part, and thus the sealing part coupled to the insertion bar closely adheres to the inner walls of the chamber body.

* * * * *